(12) United States Patent
Knudsen

(10) Patent No.: US 7,521,210 B2
(45) Date of Patent: Apr. 21, 2009

(54) METHOD FOR LARGE-SCALE PRODUCTION OF POLYPEPTIDE IN EUKARYOTE CELLS AND A CULTURE VESSEL SUITABLE THEREFOR

(75) Inventor: Ida Mølgaard Knudsen, Værløse (DK)

(73) Assignee: Novo Nordisk Healthcare A/G, Zurich (CH)

( * ) Notice: Subject to any disclaimer, the term of this patent is extended or adjusted under 35 U.S.C. 154(b) by 251 days.

(21) Appl. No.: 11/393,257

(22) Filed: Mar. 30, 2006

(65) Prior Publication Data

US 2006/0216790 A1  Sep. 28, 2006

Related U.S. Application Data

(63) Continuation of application No. PCT/DK2004/000673, filed on Oct. 6, 2004.

(60) Provisional application No. 60/512,672, filed on Oct. 20, 2003.

(51) Int. Cl.
*C12P 21/06* (2006.01)
*A61K 38/00* (2006.01)
*A61K 38/48* (2006.01)

(52) U.S. Cl. ............... 435/69.6; 530/381; 530/383; 530/384

(58) Field of Classification Search ............... None
See application file for complete search history.

(56) References Cited

U.S. PATENT DOCUMENTS

2003/0087372 A1 * 5/2003 DeLaCruz et al. ........... 435/69.1

FOREIGN PATENT DOCUMENTS

| EP | 810281 | 5/1997 |
|----|--------|--------|
| FR | 2 616 798 | 6/1987 |
| GB | 2 171 818 | 2/1986 |
| WO | 02/29083 | 4/2002 |
| WO | 02/29084 | 4/2002 |
| WO | 03/029442 | 4/2003 |

OTHER PUBLICATIONS

Pattison, R.N. et al., Biotechnol Prog., vol. 16, pp. 769-774 (2000).
Mostafa, S.S. et al., Biotechnol Prog., vol. 19, pp. 45-51 (2003).
Garnier, A. et al., Cytotechnology, vol. 22, pp. 53-63 (1996).
Payne, G.F. et al., Dev Ind Microbiol., vol. 31 (suppl5), pp. 293-301 (1990).
Frick, R. et al., J Biosci Bioeng., vol. 87 (3), pp. 344-351 (1999).
Oeggerli, A. et al., Biotechnol and Bioeng., vol. 45 (1), pp. 42-53 (1995).
Langheinrich, C. et al., Biotechnol and Bioeng., vol. 66 (3), pp. 171-179 (1999).
Vogel, J.H. et al., Papers Am Chem Soc, Abstract, vol. 224, p. Biot41 (2002).
Chisti, Y., Bioprocess Eng., vol. 9, pp. 191-196 (1993).
Van Der Pol, L.A. et al., Enzyme Microb Technol., vol. 17, pp. 401-407 (1995).
Bauer, P. et al., Biotechnol Prog., vol. 16, pp. 125-132 (2000).
McIntyre, M. et al., Appl Environ Microbiol, vol. 63 (11), pp. 4171-4177 (1997).
Backer, M.P. et al., Biotechnol and Bioeng., vol. 32 (8), pp. 993-1000 (1988).
Oh, S.K.W. et al., J Biotechnol., vol. 22 (3), pp. 245-270 (1992).
Matanguihan, R. et al., Animal Cell Tech., pp. 399-402 (2001).
Nienow, A.W. et al., Cytotechnology, vol. 22, pp. 87-94 (1996).
Osman, J.J. et al., Biotechnol Bioeng., vol. 75 (1), pp. 63-73 (2001).
Osman, J.J. et al., Biotechnol Bioeng., vol. 79 (4), pp. 398-407 (2002).
Telling, R.C. and C.J. Stone, A Method of Automatic pH Control of a Bicarbonate-$CO_2$ Buffer System for the Submerged Culture of Hamster Kidney Cells, Biotechnology and Engineering, vol. VI, pp. 147-158 (1964).
Office Action of the European Patent Office Dated Jan. 9, 2009 for EP Application 04 762 893.8 Citing the Above Reference.

* cited by examiner

*Primary Examiner*—Herbert J. Lilling
(74) *Attorney, Agent, or Firm*—Reza Green

(57) ABSTRACT

The invention provides a method for large-scale production of a polypeptide, such as a Factor VII or Factor VIIa polypeptide, in eukaryote cells, such as mammalian cells, contained in a culture liquid, said method comprising: monitoring the concentration of dissolved $CO_2$ in the culture liquid, and constantly or intermittently sparging atmospheric air through the culture liquid, wherein the sparging rate of the air is controlled in relation to the monitored concentration of dissolved $CO_2$ in the culture liquid. The method reduces or eliminates the use of bases while providing an excellent pH control. The invention also provides a culture vessel suitable for the methods.

15 Claims, 1 Drawing Sheet

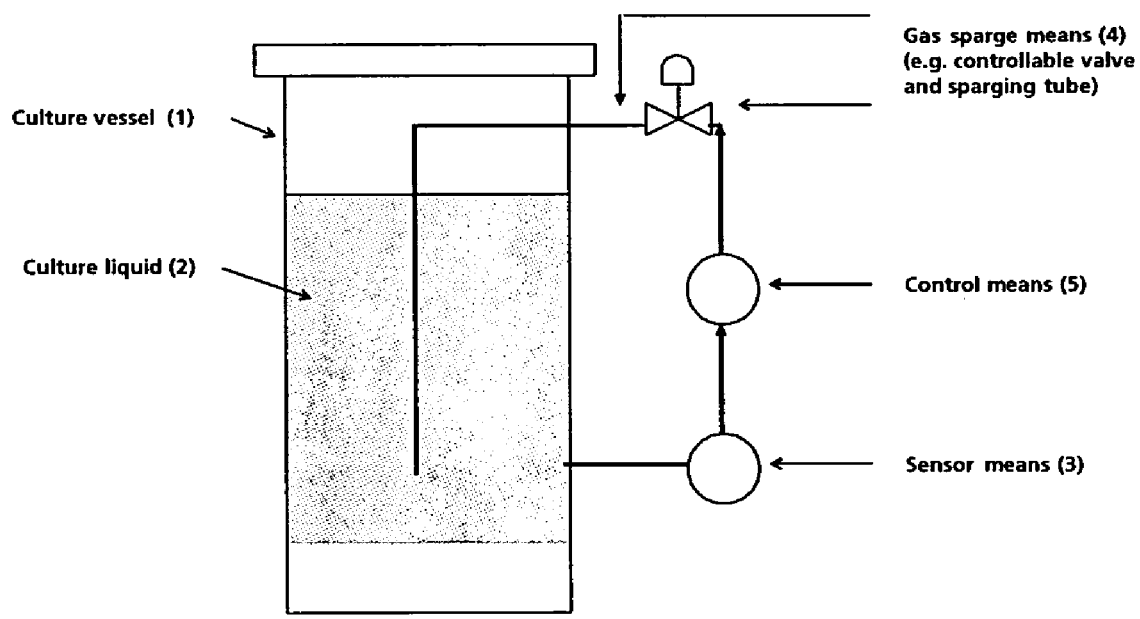

METHOD FOR LARGE-SCALE PRODUCTION OF POLYPEPTIDE IN EUKARYOTE CELLS AND A CULTURE VESSEL SUITABLE THEREFOR

FIELD OF THE INVENTION

The present invention relates to methods for producing interesting polypeptides in eukaryote cells and to a reactor vessel useful for these methods.

BACKGROUND OF THE INVENTION

Methods for large-scale production of polypeptides, such as Factor VII polypeptides, in eukaryote cells are known in the art, see, e.g., WO 02/29083, WO 02/29084 and WO 03/29442. Although many of the problems associated with large-scale production of polypeptides, such as Factor VII polypeptides, have been overcome, a few problems still remain unresolved.

Maintaining the pH value of the culture liquid within a fairly narrow optimal production "window", e.g. within 0.5 pH unit or less as it is for many cell cultures, is a particular problem. Generation of $CO_2$ and lactate in the culture liquid causes a pH decrease, and for most practical purposes, addition of strong bases, e.g. 1 M NaOH or 1M $Na_2CO_3$, is necessary in order to stabilize pH or to maintain pH within a predetermined range. Addition of strong base however causes problems with respect to a dramatic, localized pH increase which may lead to anomalous cell metabolism (high rate of glucose consumption, high rate of lactate formation), if not cell apoptosis, cf. Nienow et al., Cytotechnology 22: 87-94, 1996; Langheinrich and Nienow, Biotechnology and Bioengineering, 66 (3): 171-179, 1999; Osman et al., Biotechnology and Bioengineering, 75 (1): 63-73, 2001; and Osman et al., Biotechnology and Bioengineering, 79 (4): 398-407, 2002.

Thus, there is a need for improved methods for large-scale production of polypeptides from eukaryote cells, in particular methods where the need for addition of strong base is reduced or eliminated.

Mostafa and Gu, Biotechnol. Prog., 2003, 19, 45-51, disclose various strategies for removing dissolved $CO_2$ from large scale fed-batch cultures, e.g using sparging with air.

Pattison et al., Biotechnol. Prog., 2000, 16, 768-774, disclose measurement and control of dissolved $CO_2$ in mammalian cell culture processes using an in situ fiber optic chemical sensor. Dissolved $CO_2$ is removed by nitrogen sparging of the culture.

Although these references mention strategies for controlling the level of dissolved $CO_2$ in cell culture vessels by means of gas sparging none of them mention that the need for base addition can in this way be reduced or totally eliminated.

SUMMARY OF THE INVENTION

In one aspect, the present invention relates to a method for large-scale production of a polypeptide in eukaryote cells contained in a culture liquid, said method comprising: monitoring the concentration of dissolved $CO_2$ in the culture liquid, and constantly or intermittently sparging air through the culture liquid, wherein the sparging rate of the air is controlled in relation to the monitored concentration of dissolved $CO_2$ in the culture liquid.

In another aspect, the present invention relates to a method for large-scale production of a polypeptide in eukaryote cells contained in a culture liquid, said method comprising constantly or intermittently sparging air through the culture liquid at a rate sufficient for maintaining the concentration of dissolved $CO_2$ in the culture liquid within a predetermined range comprising a set-point for said concentration, wherein any solid or liquid substances added to the culture liquid do not give rise to a localized pH value of above 7.5 in said culture liquid.

In a further aspect, the present invention relates to a culture vessel (1) comprising a culture liquid (2), said vessel being adapted for industrial-scale production of a polypeptide in a eukaryote cell comprised in the culture liquid (2), said vessel further comprising first sensor means (3) for monitoring the concentration of dissolved $CO_2$ in the culture liquid (2), gas sparge means (4) for sparging a gas (such as air) through the culture liquid (2), and control means (5), said control means (5) being in communication with said first sensor means (3), and said control means (5) being in communication with said gas sparge means (4), wherein the control means (5) controls the sparge rate of the gas via the gas sparge means (4) in response to the value of dissolved $CO_2$ monitored by the first sensor means (3).

BRIEF DESCRIPTION OF THE DRAWINGS

FIG. 1 illustrates a non-limiting embodiment of the reactor vessel of the invention.

DETAILED DESCRIPTION OF THE INVENTION

Methods

One aspect of the present invention relates to methods for large-scale production of a polypeptide in eukaryotic cells contained in a culture liquid. A feature of the methods is that air is sparged constantly or intermittently through the culture liquid for $CO_2$ and pH control so as to reduce or eliminate the need for addition of bases.

Thus in a principal embodiment, the present invention provides a method for large-scale production of a polypeptide in eukaryote cells contained in a culture liquid, said method comprising: monitoring the concentration of dissolved $CO_2$ in the culture liquid, and constantly or intermittently sparging air through the culture liquid, wherein the sparging rate of the air is controlled in relation to the monitored concentration of dissolved $CO_2$ in the culture liquid.

By the term "large-scale production" is meant production involving a culture vessel of at least 100 L. In preferred embodiments, however, the scale is typically at least 250 L, such as at least 500 L, e.g. at least 1000 L or even 5000 L or more. The term "large-scale" may be used interchangeably with the terms "industrial-scale" and "production-scale".

The method for large-scale production of the polypeptide is typically conducted over a period of at least 120 hours, e.g. 1-26 weeks.

The present invention is currently not limited to the production of any particular polypeptide or to the use of any particular eukaryotic cell. However, illustrative examples of relevant polypeptides and useful eukaryotic cells are provided further below. However, in some of the currently most interesting and preferred embodiments of the invention, the polypeptide is a Factor VII polypeptide.

The term "culture liquid" is intended to mean a liquid comprising a culture of the eukaryotic cells in a suitable medium. In one important embodiment, the cells are immobilized by attachment onto the surface of solid microcarriers or by attachment to or physical entrapment inside the internal structure of macroporous microcarriers. This embodiment will be explained in further details further below.

The method of the invention involves monitoring the concentration of dissolved $CO_2$ in the culture liquid and sparging of air, either constantly or intermittently, through the culture liquid. The sparging rate of the air is controlled in relation to the monitored concentration of dissolved $CO_2$ in the culture liquid.

Monitoring of gases, including $CO_2$, in liquids is known in the art, and a number of sensors are commercially available (see "Culture Vessel"). Such $CO_2$ sensors typically provide an electrical signal carrying data corresponding to the actual concentration value. Some sensors further provide a read-out of the actual value for the concentration of dissolved $CO_2$. The read-out or electrical signal can be used for controlling the sparging rate of air to the culture liquid. Although such control may be conducted manually, the preferred embodiment includes employment of automatic control. The automatic control is typically conducted by a control means and typically involves a predetermined algorithm. One useful culture vessel for the above method is described further below (see "Culture Vessel").

The sparging rate is controlled in relation to the monitored concentration of $CO_2$ so that a significant increase in the actual (monitored) concentration of dissolved $CO_2$ (relative to a predefined set-point) is countered by an increase in the sparging rate of the air, and so that a significant decrease in the actual (monitored) concentration of dissolved $CO_2$ (relative to a predefined set-point) is countered by a decrease in the sparging rate of the air. In this way, the method preferably renders it possible to keep the concentration of dissolved $CO_2$ within a predetermined range comprising a set-point for said concentration.

The set-point is typically defined by the operator prior to monitoring the concentration of dissolved $CO_2$ and is the concentration at which the operator considers the production of the polypeptide in the eukaryotic cells to be optimal. In certain instances the set-point may be slightly adjusted in the course of the production phase so as to take any alterations in the culture liquid into account.

Examples of algorithms for controlling the sparging rate in relation to the concentration of dissolved $CO_2$ include on-off control, proportional control (P), proportional-derivative (PD) control, proportional-integral (PI) control and proportional-integral-derivative (PID) control, of which PI and PID control often are preferred. For further details see, e.g., Michael Barr, "Closed-Loop Control", Embedded Systems Programming, August 2002, pp. 55-56, and www-.neutrino.com/Publications/Glossary/PID.html.

The range of the concentration of dissolved $CO_2$ at which the production of the polypeptide is feasible, and the set-point at which the production is considered optimal is somewhat dependent of the polypeptide in question, the selected eukaryotic cell, and the medium, thus, the skilled person will be able to determine this range and this value by standard experimentation.

However in some important embodiments, the predetermined range for the concentration of dissolved $CO_2$ is typically 80-200 mmHg, in particular 100-180 mmHg. The set-point concentration of dissolved $CO_2$ in the culture liquid is typically a value in the range of 100-180 mmHg, such as 120-160 mmHg, e.g. a value of around 140 mmHg.

The term "sparging rate of air" is expressed in L/min per L of culture liquid (volume per volume per minute (vvm)), and is defined as the rate at which air, normalized to a temperature of 25° C. and a pressure of 1 atm (101.3 kPa), is fed to the culture liquid.

The term "constantly or intermittently" is intended to mean that the sparging of air can be conducted in any manner, e.g. by a substantially uninterrupted (i.e. constant) flow of the air or an intermittent flow of air, etc. The sparging rate for an intermittent flow of air is calculated as the average flow rate (L/min) over a period of 3 minutes, i.e. the flow in litres over the preceding 3 minutes divided by 3. Preferably, the sparging of air is conducted substantially uninterrupted. This is advantageous because the sparging of air also facilitates the mixing within the culture vessel.

The term "air" is intended to cover gases comprising 60-90%, such as 65-85% (e.g. 75-82%), nitrogen, 10-40%, such as 15-35% (e.g. 18-24%), oxygen, and less than 0.5% (e.g. less than 0.2%) $CO_2$. The "air" can be obtained by mixing atmospheric air with nitrogen/or oxygen in a suitable ratio. A preferred example hereof is atmospheric air which comprises approx. 78% nitrogen, approx. 21% oxygen, and less than 0.1% $CO_2$. Use of air provides the advantage of supplying oxygen to the culture liquid while at the same time removing $CO_2$ from the culture liquid.

In view of the results obtained so far, the sparging rate of air is preferably in the range of 0.000-0.100, such as 0.000-0.070 L/min per L of culture liquid. In particular, the sparging rate of air is typically in the range of 0.005-0.020 L/min per L of culture liquid when the monitored concentration of dissolved $CO_2$ is equal to the set-point concentration.

In preferred embodiments, the sparging rate of air is: in the range of 0.000-0.005, such as around 0.0 L/min per L of culture liquid when the monitored concentration of dissolved $CO_2$ is equal to the set-point concentration−5 mmHg; and in the range of 0.010-0.100, such as 0.030-0.070, e.g. around 0.040-0.060, L/min per L of culture liquid when the monitored concentration of dissolved $CO_2$ is equal to the set-point concentration+5 mmHg.

The present invention provides a useful way of controlling the concentration of dissolved $CO_2$ in the culture liquid and thereby also indirectly controlling pH in the culture liquid. The present invention therefore provides a measure for reducing or eliminating the need for addition of bases.

Thus, in one interesting embodiment, any solid or liquid substances added to the culture liquid do not give rise to a localized pH value of above 7.5 in said culture liquid. Preferably, no bases with a pH value of above 8.5 are added to the culture liquid.

The term "localized pH value" refers to the phenomenon arising where addition of, e.g., even a small amount of a strong base (e.g. pH 10) to a culture liquid (e.g. pH about 7.0) causes the pH value to increase locally to, e.g., 9.0 before the strong base is thoroughly mixed with the culture medium. In some instances, mixing may further cause a local temperature increase if the mixing process is exothermic. The term "any solid or liquid substances added to the culture liquid" refers to and includes all agents, media, solutions, suspensions, etc. added to the culture liquid during production of the polypeptide.

In a particular variant of the invention, it is envisaged that actual on-line monitoring of the concentration of dissolved $CO_2$ may not be strictly mandatory. Thus, the present invention also provides a method for large-scale production of a polypeptide in eukaryote cells contained in a culture liquid, said method comprising constantly or intermittently sparging air through the culture liquid at a rate sufficient for maintaining the concentration of dissolved $CO_2$ in the culture liquid within a predetermined range comprising a set-point for said concentration, wherein any solid or liquid substances added to the culture liquid do not give rise to a localized pH value of above 7.5 in said culture liquid. The concentration of dissolved $CO_2$ may be monitored off-line by analyzing samples of the culture liquid with a conventional gas analyzing equipment, e.g. a commercial blood-gas analyzer.

In this embodiment, the sparging rate of air is typically in the range of 0.001-0.070, such as 0.005-0.020, L/min per L of culture liquid. Furthermore, the concentration of dissolved $CO_2$ in the culture liquid is preferably monitored in order to ensure that the concentration of dissolved $CO_2$ in the culture liquid is maintained within the predetermined range. Alternatively pH is monitored.

In this embodiment, the sparging rate of air is preferably controlled in relation to the monitored concentration of $CO_2$. Alternatively, the sparging rate of air may be controlled in relation to the monitored pH. In particular, the sparging rate may be controlled in relation to the monitored pH and monitored lactate concentration.

In particular, the sparging rate of air is in the range of 0.005-0.020 L/min per L of culture liquid when the monitored concentration of dissolved $CO_2$ is equal to the set-point concentration. Furthermore, the sparging rate of air is typically:

in the range of 0.000-0.005, such as around 0.0 L/min per L of culture liquid when the monitored concentration of dissolved $CO_2$ is equal to the set-point concentration−5 mmHg; and in the range of 0.010-0.100, such as 0.030-0.070, e.g. around 0.040-0.060, L/min per L of culture liquid when the monitored concentration of dissolved $CO_2$ is equal to the set-point concentration+5 mmHg.

Culture Vessel

The present invention also provides a culture vessel particularly useful for the methods of the invention.

The culture vessel (1) comprises a culture liquid (2), said vessel being adapted for industrial-scale production of a polypeptide in a eukaryote cell comprised in the culture liquid (2), said vessel further comprising first sensor means (3) for monitoring the concentration of dissolved $CO_2$ in the culture liquid (2), gas sparge means (4) for sparging a gas (such as air) through the culture liquid (2), and control means (5), said control means (5) being in communication with said first sensor means (3), and said control means (5) being in communication with said gas sparge means (4), wherein the control means (5) controls the sparge rate of the gas via the gas sparge means (4) in response to the value of dissolved $CO_2$ monitored by the first sensor means (3).

One embodiment of the culture vessel of the invention is illustrated in FIG. 1.

The first sensor means (3) is particularly adapted to constantly or intermittently monitor the concentration of dissolved $CO_2$ in the culture liquid (2). Such sensor means are commercially available from various commercial suppliers, e.g. the YSI 8500 fiber optic $dCO_2$ sensor from YSI, Inc.

The gas sparge means (4) can, e.g., be selected from controllable valves, controllable pumps, etc. and combinations of valves and pumps. Such valves and/or pumps brings air, e.g. pressurized air, into the culture liquid at a rate controlled by the control means (5) based on the concentration value for dissolved $CO_2$ in the culture liquid. Such gas sparge means are commercially available from various commercial suppliers, e.g. Burkert, HI-TEC, Samson, Emerson.

In one embodiment, the sparge rate of the gas can be controlled so as to maintain the concentration of dissolved $CO_2$ in the culture liquid within a predetermined range comprising a set-point for said concentration. In particular, the gas sparge means is adapted to provide sparge rates of 0.000-0.100, such as 0.000-0.050, L/min per L of culture liquid.

The control means (5) is typically a microprocessor-containing device which is capable of receiving signals or data from the first sensor means (3) and providing signals or data to the gas sparge means (4). Control means are commercially available from various commercial suppliers, e.g. Philips, Yokogawa, Honeywell.

Suitable algorithms for implementation in the control means are described further above.

The term "in communication with" means that digital and/or analogous signals and data can be exchanged between the respective "means", or from one "means" to another. The communication may be directly via electrical wires or, where applicable, via transmitters and transducers of electromagnetic radiation, infrared radiation, etc.

The control means (5) typically comprises presetting means so that an operator of the culture vessel is able to enter the end-points for the predetermined range and the predetermined set-point for the concentration of dissolved $CO_2$ in the culture liquid. The end-points for the range and the set-point may optionally be modified in the course of the operation of the culture vessel, if necessary or desirable.

Modifications of the first sensor means (3), the gas sparge means (4), the control means (5) and the way of bringing these into communication with each other will be apparent for the person skilled in the art.

Culture vessels applicable within the present invention may, e.g., be based on conventional stirred tank reactors (CSTR) where agitation is obtained by means of conventional impeller types or airlift reactors where agitation is obtained by means of introducing air from the bottom of the vessel. Among the further parameters that are typically controlled within specified limits are pH, dissolved oxygen tension (DOT), and temperature. Dissolved oxygen tension may be maintained by, e.g., sparging with pure oxygen. The temperature-control medium is typically water, heated or cooled as necessary. The water may be passed through a jacket surrounding the vessel or through a piping coil immersed in the culture.

The term "culture vessel" may be used interchangeably with "tank", "reactor", "fermentor" and "bioreactor".

Polypeptides for Large-Scale Production

The present invention relates to methods relevant for the improved large-scale cultivation of eukaryote cells that express one or more proteins of interest, whether from endogenous genes or subsequent to introduction into such cells of recombinant genes encoding the protein. Such proteins include, without limitation, Factor VII polypeptides; Factor VIII; Factor IX; Factor X; Protein C; tissue factor; rennin; growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β platelet-derived growth factor (PDGF); fibroblast growth factor such as α-FGF and β-FGF; epidermal growth factor (EGF); transforming growth factor (TGF) such as TGF-alpha and TGF-beta, insulin-like growth factor-I and -II (IGF-I and IGF-II); CD proteins such as CD-3, CD-4, CD-8, and CD-19; erythropoietin; osteoinductive factors; immunotoxins; bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressin; regulatory proteins; antibodies; and sequence variants and fragments of any of the above polypeptides.

In preferred embodiments of the invention, the polypeptide is a Factor VII polypeptide.

In some embodiments hereof, the cells used in practicing the invention are human cells expressing an endogenous Factor VII gene. In these cells, the endogenous gene may be intact or may have been modified in situ, or a sequence outside the Factor VII gene may have been modified in situ to alter the expression of the endogenous Factor VII gene.

In other embodiments hereof, cells from any eukaryote source are engineered to express human Factor VII from a recombinant gene.

"Factor VII polypeptide" encompasses wild-type Factor VII (i.e. a polypeptide having the amino acid sequence disclosed in U.S. Pat. No. 4,784,950), as well as variants of Factor VII exhibiting substantially the same or improved biological activity relative to wild-type Factor VII, and Factor VII variants having substantially modified or reduced biological activity relative to wild-type Factor VII. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. The term "Factor VII polypeptide" also encompasses polypeptides, including variants, in which the Factor VIIa biological activity has been substantially modified or somewhat reduced relative to the activity of wild-type Factor VIIa. These polypeptides include, without limitation, Factor VII or Factor VIIa into which specific amino acid sequence alterations have been introduced that modify or disrupt the bioactivity of the polypeptide.

The biological activity of Factor VIIa in blood clotting derives from its ability to (i) bind to Tissue Factor (TF) and (ii) catalyze the proteolytic cleavage of Factor IX or Factor X to produce activated Factor IX or X (Factor IXa or Xa, respectively).

Biological activity of Factor VII polypeptides ("Factor VII biological activity") may be quantified by measuring the ability of a preparation to promote blood clotting using Factor VII-deficient plasma and thromboplastin, as described, e.g., in U.S. Pat. No. 5,997,864 or WO 92/15686. In this assay, biological activity is expressed as the reduction in clotting time relative to a control sample and is converted to "Factor VII units" by comparison with a pooled human serum standard containing 1 unit/mL Factor VII activity. Alternatively, Factor VIIa biological activity may be quantified by (i) measuring the ability of Factor VIIa (or the Factor VII polypeptide) to produce activated Factor X (Factor Xa) in a system comprising TF embedded in a lipid membrane and Factor X. (Persson et al., J. Biol. Chem. 272:19919-19924, 1997); (ii) measuring Factor X hydrolysis in an aqueous system ("In Vitro Proteolysis Assay", Assay 2—see below); (iii) measuring the physical binding of Factor VIIa (or the Factor VII polypeptide) to TF using an instrument based on surface plasmon resonance (Persson, FEBS Letts. 413:359-363, 1997); (iv) measuring hydrolysis of a synthetic substrate by Factor VIIa (or a Factor VII polypeptide) ("In Vitro Hydrolysis Assay", Assay 1—see below); or (v) measuring generation of thrombin in a TF-independent in vitro system.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); Factor VIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); Factor VII variants as disclosed in PCT/DK02/00189; and Factor VII variants exhibiting increased proteolytic stability as disclosed in WO 02/38162 (Scripps Research Institute); Factor VII variants having a modified Gla-domain and exhibiting an enhanced membrane binding as disclosed in WO 99/20767 (University of Minnesota); and Factor VII variants as disclosed in WO 01/58935 (Maxygen ApS).

Non-limiting examples of Factor VII variants having increased biological activity compared to wild-type Factor VIIa include Factor VII variants as disclosed in WO 01/83725, WO 02/22776, WO 02/077218, WO 03/27147, WO 03/37932; WO 02/38162 (Scripps Research Institute); and Factor VIIa variants with enhanced activity as disclosed in JP 2001061479 (Chemo-Sero-Therapeutic Res Inst.).

Non-limiting examples of Factor VII variants having substantially reduced or modified biological activity relative to wild-type Factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Hoist et al., Eur. J. Vasc. Endovasc. Surg. 15:515-520, 1998), and Factor VIIa lacking the Gla domain, (Nicolaisen et al., FEBS Letts. 317:245-249, 1993).

Explicit examples of Factor VII polypeptides include, without limitation, wild-type Factor VII, L305V-FVII, L305V/M306D/D3095-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, 5314E/K316H-FVII, 5314E/K316Q-FVII, 5314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T/S314E-FVII, F374Y/V158D/E296V/M298Q/K337A/S314E-FVII, F374Y/L305V/

V158D/E296V/M298Q/S314E-FVII, F374Y/L305V/
E296V/M298Q/V158T/S314E-FVII, F374Y/L305V/
E296V/M298Q/K337A/V158T-FVII, F374Y/L305V/
E296V/K337A/V158T/S314E-FVII, F374Y/L305V/
M298Q/K337A/V158T/S314E-FVII, F374Y/L305V/
V158D/E296V/M298Q/K337A-FVII, F374Y/L305V/
V158D/E296V/K337A/S314E-FVII, F374Y/L305V/
V158D/M298Q/K337A/S314E-FVII, F374Y/L305V/
E296V/M298Q/K337A/V158T/S314E-FVII, F374Y/
L305V/V158D/E296V/M298Q/K337A/S314E-FVII,
S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/V317T-FVII, K143N/N145T/R315N/V317T-FVII; and Factor VII having substitutions, additions or deletions in the amino acid sequence from 233Thr to 240Asn, Factor VII having substitutions, additions or deletions in the amino acid sequence from 304Arg to 329Cys.

In some embodiments, the Factor VII polypeptide is human Factor VIIa (hFVIIa), preferably recombinantly made human Factor VIIa (rhFVIIa).

In other embodiments, the Factor VII polypeptide is a Factor VII sequence variant.

In some embodiments, e.g. those where the Factor VII polypeptide is a Factor VII sequence variant, the ratio between the activity of the Factor VII polypeptide and the activity of native human Factor VIIa (wild-type FVIIa) is at least about 1.25, preferably at least about 2.0, or at least about 4.0, when tested in the "In Vitro Proteolysis Assay" (Assay 2) as described in the present specification.

In some embodiments, e.g. those where the Factor VII polypeptide is a Factor VII sequence variant, the ratio between the activity of said Factor VII polypeptide and the activity of native human Factor VIIa (wild-type FVIIa) is at least about 1.25, preferably at least about 2.0, or at least about 4.0, when tested in the "In Vitro Hydrolysis Assay" (Assay 1) as described in the present specification.

In some embodiments, the Factor VII polypeptide has a glycosylation different from wild-type human Factor VII.

Cells

In practising the present invention, the cells are eukaryote cells, more preferably an established eukaryote cell line, including, without limitation, CHO (e.g., ATCC CCL 61), COS-1 (e.g., ATCC CRL 1650), baby hamster kidney (BHK), and HEK293 (e.g., ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk⁻ ts13 BHK cell line is also available from the ATCC under accession number CRL 1632. A preferred CHO cell line is the CHO K1 cell line available from ATCC under accession number CCl61.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1); DUKX cells (CHO cell line) (Urlaub and Chasin, *Proc. Natl. Acad. Sci. USA* 77:4216-4220, 1980) (DUKX cells also being referred to as DXB11 cells), and DG44 (CHO cell line) (*Cell*, 33: 405, 1983, and *Somatic Cell and Molecular Genetics* 12: 555, 1986). Also useful are 3T3 cells, Namalwa cells, myelomas and fusions of myelomas with other cells. In some embodiments, the cells may be mutant or recombinant cells, such as, e.g., cells that express a qualitatively or quantitatively different spectrum of enzymes that catalyze post-translational modification of proteins (e.g., glycosylation enzymes such as glycosyl transferases and/or glycosidases, or processing enzymes such as propeptides) than the cell type from which they were derived. Suitable insect cell lines also include, without limitation, Lepidoptera cell lines, such as *Spodoptera frugiperda* cells or *Trichoplusia ni* cells (see, e.g., U.S. Pat. No. 5,077,214).

In some embodiments, the cells used in practising the invention are capable of growing in suspension cultures. As used herein, suspension-competent cells are those that can grow in suspension without making large, firm aggregates, i.e., cells that are monodisperse or grow in loose aggregates with only a few cells per aggregate. Suspension-competent cells include, without limitation, cells that grow in suspension without adaptation or manipulation (such as, e.g., haematopoietic cells or lymphoid cells) and cells that have been made suspension-competent by gradual adaptation of attachment-dependent cells (such as, e.g., epithelial or fibroblast cells) to suspension growth.

The cells used in practising the invention may be adhesion cells (also known as anchorage-dependent or attachment-dependent cells). As used herein, adhesion cells are those that need to adhere or anchor themselves to a suitable surface for propagation and growth. In one embodiment of the invention, the cells used are adhesion cells. In these embodiments, both the propagation phases and the production phase include the use of microcarriers. The used adhesion cells should be able to migrate onto the carriers (and into the interior structure of the carriers if a macroporous carrier is used) during the propagation phase(s) and to migrate to new carriers when being transferred to the production bioreactor. If the adhesion cells are not sufficiently able to migrate to new carriers by themselves, they may be liberated from the carriers by contacting the cell-containing microcarriers with proteolytic enzymes or EDTA. The medium used (particularly when free of animal-derived components) should furthermore contain components suitable for supporting adhesion cells; suitable media for cultivation of adhesion cells are available from commercial suppliers, such as, e.g., Sigma.

The cells may also be suspension-adapted or suspension-competent cells. If such cells are used, the propagation of cells may be done in suspension, thus microcarriers are only used in the final propagation phase in the production culture vessel itself and in the production phase. In case of suspension-adapted cells the microcarriers used are typically macroporous carriers wherein the cells are attached by means of physical entrapment inside the internal structure of the carriers.

Cell Culture Procedures

The methods of the invention are typically performed in a stirred culture vessel and a microcarrier-based process type is preferably employed. In the microcarrier-based process the cells have migrated into the internal structure of the carriers (macroporous carriers) or have attached themselves to the surface of the carriers (solid carriers), or both. In a microcarrier-based process the eukaryote cells, the microcarriers and the culture medium are supplied to a culture vessel initially. In the following days additional culture medium may be fed if the culture volume was not brought to the final working volume of the vessel from the start. During the following period periodic harvest of product-containing culture supernatant and replacement with new medium is performed, until the culture is finally terminated. When harvesting product-containing supernatant the agitation, e.g., stirring, of the culture is stopped and the cell-containing carriers are allowed to sediment following which part of the product-containing culture medium is removed.

In order to improve the overall outcome of the procedure, a cooling step may preferably be applied before harvesting of the product-containing supernatant, see, e.g., WO 03/029442. In some embodiments the culture liquid is cooled to a temperature between about 18° C. and about 32° C. before allowing the carriers to sediment, or between about 20° C. and about 30° C., or between about 22° C. and about 28° C.

Other applicable variants of the cell culture procedure are disclosed in WO 02/29084.

Propagation Steps

Before reaching the production phase where regular harvesting of product-containing culture supernatant for further down-stream processing is performed, the cells are propagated according to any scheme or routine that may be suitable for the particular cell in question. The propagation phase may be a single step or a multiple step procedure. In a single step propagation procedure the cells are removed from storage and inoculated directly to the culture vessel containing the microcarriers where the production is going to take place. In a multiple step propagation procedure the cells are removed from storage and propagated through a number of culture vessels of gradually increasing size until reaching the final culture vessel containing microcarriers where production is going to take place. During the propagation steps the cells are grown under conditions that are optimized for growth. Culture conditions, such as temperature, pH, dissolved oxygen tension and the like, are those known to be optimal for the particular cell and will be apparent to the skilled person or artisan within this field (see, e.g., *Animal Cell Culture: A Practical Approach* $2^{nd}$ Ed., Rickwood, D. and Hames, B. D., eds., Oxford University Press, New York (1992)).

In one approach, the cell culture process is operated in one culture vessel: The cells are inoculated directly into the culture vessel containing microcarriers where the production is going to take place; the cells are propagated until a suitable cell density is reached and the production phase is initiated.

In another approach, the cell culture process is operated in at least two distinct culture vessels: One or more seed culture vessel(s) (first propagation step(s)) followed by the production culture vessel (last propagation step followed by production phase). In the first propagation step the cells expressing the desired polypeptide are inoculated into a seed culture vessel containing culture medium and propagated until the cells reach a minimum cross-seeding density. Subsequently, the propagated seed culture is transferred to the production culture vessel containing (a) culture medium and (b) microcarriers. In this culture vessel the cells are cultured under conditions in which the cells migrate onto the surface of the solid carriers or the exterior and interior surfaces of the macroporous carriers, and they continue to grow in this last propagation step until the carriers are fully colonised by the cells. During this last propagation step medium exchange is performed by allowing the microcarriers to settle to the bottom of the culture vessel, after which a predetermined percentage of the tank volume is removed and a corresponding percentage tank volume of fresh medium is added to the vessel. The microcarriers are then re-suspended in the medium and this process of medium removal and replacement are repeated at a predetermined interval, for example every 24 hours. The amount of replaced medium depends on the cell density and may typically be from 10% to 95%, preferably from 25% to 80%, of the tank volume as shown in Table 1 below.

It will be understood that in a process where the propagation phase is a multiple step procedure the propagation may take place in culture vessels of progressively increasing size until a sufficient number of cells is obtained for entering the final culture vessel. For example, one or more seed culture vessels of 5 L, 50 L, 100 L or 500 L may be used sequentially. A seed culture vessel typically has a capacity of between 5 L and 1000 L. Typically, cells are inoculated into a seed culture vessel at an initial density of about 0.2 to $0.4 \times 10^6$ cells/mL and propagated until the culture reaches a cell density of about $1.0 \times 10^6$ cells/mL. Typically, a minimum cross-seeding density is between about 0.8 and about $1.5 \times 10^6$ cells/mL.

Some of the set-points that are suitable for the production of a desired polypeptide, e.g., factor VII, are not necessarily suitable for the initial growth of the cells, either in seed culture or on the microcarriers. For example, temperature, dissolved oxygen tension, and/or pH may be different for the two phases. The medium exchanges during propagation is done to keep the cells alive and growing, not to harvest culture supernatant for down-stream processing.

Possible culture conditions for the last propagation step in the final culture vessel (containing microcarriers) are outlined in Table 1, below.

TABLE 1

| Set-point | Range | Preferred range | More preferred Value |
|---|---|---|---|
| Dissolved CO2 | 80-200 mmHg | 100-180 mmHg | 120-160 mmHg |
| pH | 6-8 | 6.6-7.6 | 7.0 |
| Temperature | 28-40° C. | 34-38° C. | 36-37° C. |
| Dissolved Oxygen Tension | 10-90% of saturation | 20-80% of saturation | 50% of saturation |
| Daily Medium Change: | | | |
| % of medium changed at | 10-35% of medium exchanged at $0.4\text{-}1.0 \times 10^6$ cells/mL | 25% of medium exchanged at $0.4\text{-}1.0 \times 10^6$ cells/mL | 25% of medium exchanged at $0.5 \times 10^6$ cells/mL |
| % of medium changed at | 30-70% of medium exchanged at $0.7\text{-}3.0 \times 10^6$ cells/mL | 50% of medium exchanged at $0.7\text{-}3.0 \times 10^6$ cells/mL | 50% of medium exchanged at $1.0 \times 10^6$ cells/mL |
| % of medium changed at | 60-90% of medium exchanged at $1.0\text{-}12.0 \times 10^6$ cells/mL | 80% of medium exchanged at $1.0\text{-}12.0 \times 10^6$ cells/mL | 80% of medium exchanged at $2.0\text{-}10 \times 10^6$ cells/mL |

Production Phase

The methods of the present invention are primarily interesting for the production phase, although they may be utilised for the propagation phase if desirable (see Table 1).

Besides the features and measures defined for the methods of the present invention, a number of other measures need to be taken for the production to yield a satisfactory outcome as will be described in the following.

When the cell density reaches the value suitable for start of production phase, i.e. for having product-containing culture supernatant down-stream processed, 60-95% of the culture supernatant is harvested every 24 hours, preferably 80%. This value of cell density is typically $1-12\times10^6$ cells/mL. Set-points may be changed at this point and set at values suitable for production of the desired polypeptide.

The medium exchange is performed by allowing the microcarriers to settle to the bottom of the tank, after which the selected percentage of the tank volume is removed and a corresponding percentage tank volume of fresh medium is added to the vessel. Between 25 and 90% of the tank volume are typically replaced; preferably, 80% of the tank volume is replaced with fresh medium. The microcarriers are then re-suspended in the medium and this process of medium removal and replacement are typically repeated every 10 to 48 hours; preferably, every 24 hours.

An outline of this aspect of the process is shown in Table 2.

TABLE 2

| Set-point | Range | Preferred range | More preferred Value |
| --- | --- | --- | --- |
| Dissolved $CO_2$ | 80-200 mmHg | 100-180 mmHg | 120-160 mmHg |
| pH | 6-8 | 6.6-7.6 | 7.0 for CHO and 6.7-6.9 for BHK |
| Temperature | 26-40° C. | 30-37° C. | 36° C. |
| Dissolved Oxygen Tension | 10-90% of saturation | 20-80% of saturation | 50% |
| % of medium changed | 25-90% of medium exchanged every 10-48 hours | 80% of medium changed every 10-48 hours | 80% of medium changed every 24 hours |

Optionally, a drop in temperature set point of the cultivation may be employed when entering, and during, the production phase.

When entering the production phase temperature, operating pH and medium exchange frequency are typically changed to values that are optimal for production. Examples of temperature ranges and values in growth and production phase, respectively, can be seen from Tables 1 and 2. A temperature of about 36° C. is preferred for a CHO cell line during the production phase.

Microcarriers

As used herein, microcarriers are particles which are small enough to allow them to be used in suspension cultures (with a stirring rate that does not cause significant shear damage to cells). They are solid, porous, or have a solid core with a porous coating on the surface. Microcarriers may, for example, without limitation, be cellulose- or dextran-based, and their surfaces (exterior and interior surface in case of porous carriers) may be positively charged. Further details can be found in WO 02/29083.

In one series of embodiments, the microcarriers have an overall particle diameter between about 150 and 350 um; and have a positive charge density of between about 0.8 and 2.0 meq/g. In one series of embodiments, the microcarrier is a solid carrier. Useful solid microcarriers include, without limitation, Cytodex 1™ and Cytodex 2™ (Amersham Pharmacia Biotech, Piscataway N.J.). Solid carriers are particularly suitable for adhesion cells (anchorage-dependent cells).

In another series of embodiments, the microcarrier is a macroporous carrier. As used herein, macroporous carriers are particles, e.g. cellulose-based, which have the following properties: (a) They are small enough to allow them to be used in suspension cultures (with a stirring rate that does not cause significant shear damage to cells); and (b) they have pores and interior spaces of sufficient size to allow cells to migrate into the interior spaces of the particle. Their surfaces (exterior and interior) may in one embodiment be positively charged. In one series of embodiments, the carriers: (a) have an overall particle diameter between about 150 and 350 um; (b) have pores having an average pore opening diameter of between about 15 and about 40 um; and (c) have a positive charge density of between about 0.8 and 2.0 meq/g. In some embodiments, the positive charge is provided by DEAE (N,N,-diethylaminoethyl) groups. Useful macroporous carriers include, without limitation, Cytopore 1™ and Cytopore 2™ (Amersham Pharmacia Biotech, Piscataway N.J.). Particularly preferred are Cytopore 1™ carriers, which have a mean particle diameter of 230 um, an average pore size of 30 um, and a positive charge density of 1.1 meq/g.

Large-Scale Culture Conditions

As used herein, a large-scale culture vessel has a capacity of at least about 100 L, preferably at least about 500 L, more preferably at least about 1000 L and most preferably at least about 5000 L. In case that the cell culture process is operated in at least two distinct culture vessels, such as one or more seed culture vessel(s) (first propagation step(s)) followed by the production culture vessel (last propagation step followed by production phase), then the process typically involves transferring about 50 L of the propagated seed culture (having about $1.0\times10^6$ cells/mL) into a 500 L culture vessel containing 150 L of culture medium. The large-scale culture is maintained under appropriate conditions of, e.g., temperature, pH, dissolved oxygen tension (DOT), and agitation rate, and the volume is gradually increased by adding medium to the culture vessel. In case of a microcarrier process the culture vessel also comprises an amount of microcarriers corresponding to a final microcarrier concentration in the range of 1 to 10 g/L. After the transfer, the cells typically migrate onto the surface of the carriers or into the interior of the carriers within the first 24 hours.

Medium

The terms "cell culture medium" and "culture medium" (or simply "medium") refer to a nutrient solution used for growing eukaryote cells that typically provides at least one component from one or more of the following categories: (1) salts of e.g. sodium, potassium, magnesium, and calcium contributing to the osmolality of the medium; (2) an energy source, usually in the form of a carbohydrate such as glucose; (3) all essential amino acids, and usually the basic set of twenty amino acids; (4) vitamins and/or other organic compounds required at low concentrations; and (5) trace elements, where trace elements are defined as inorganic compounds that are typically required at very low concentrations, usually in the micromolar range. The nutrient solution may optionally be supplemented with one or more of the components from any of the following categories: (a) animal serum; (b) hormones and other growth factors such as, for example, insulin, transferrin, and epidermal growth factor; and (c) hydrolysates of protein and tissues.

The present invention encompasses cultivating eukaryote cells in medium comprising animal-derived components, e.g. serum or serum components, as well as medium lacking animal-derived components. The cell culture medium comprising animal-derived components (such as, e.g., fetal bovine serum (FBS)) may comprise more than 5% serum or between 0% to 5% serum, such as, for example, between 0% to 1% serum or 0% to 0.1% serum.

Medium lacking animal-derived components are preferred. As used herein, "animal-derived" components are any components that are produced in an intact animal (such as, e.g., proteins isolated and purified from serum), or produced by using components produced in an intact animal (such as, e.g., an amino acid made by using an enzyme isolated and purified from an animal to hydrolyse a plant source material). By contrast, a protein which has the sequence of an animal protein (i.e., has a genomic origin in an animal) but which is produced in vitro in cell culture (such as, e.g., in a recombinant yeast or bacterial cell or in an established continuous eukaryote cell line, recombinant or not), in media lacking components that are produced in, and isolated and purified from an intact animal is not an "animal-derived" component (such as, e.g., insulin produced in a yeast or a bacterial cell, or insulin produced in an established mammalian cell line, such as, e.g., CHO, BHK or HEK cells, or interferon produced in Namalwa cells). For example, a protein which has the sequence of an animal protein (i.e., has a genomic origin in an animal) but which is produced in a recombinant cell in media lacking animal derived components (such as, e.g., insulin produced in a yeast or bacterial cell) is not an "animal-derived component". Accordingly, a cell culture medium lacking animal-derived components is one that may contain animal proteins that are recombinantly produced; such medium, however, does not contain, e.g., animal serum or proteins or other products purified from animal serum. Such medium may, for example, contain one or more components derived from plants. Any cell culture medium, in particular one lacking animal-derived components, that supports cell growth and maintenance under the conditions of the invention may be used. Typically, the medium contains water, an osmolality regulator, a buffer, an energy source, amino acids, an inorganic or recombinant iron source, one or more synthetic or recombinant growth factors, vitamins, and cofactors. In one embodiment, the medium lacks animal-derived components and lacks proteins ("protein-free"). Media lacking animal-derived components and/or proteins are available from commercial suppliers, such as, for example, Sigma, JRH Biosciences, Gibco and Gemini.

In addition to conventional components, a medium suitable for producing factor VII or factor VII-related polypeptides contains Vitamin K, which is required for γ-carboxylation of glutamic acid residues in factor VII, at a concentration between about 0.1 to 50 mg/Litre, preferably between about 0.5 to 25 mg/Litre, more preferably between about 1 to 10 mg/Litre and most preferably about 5 mg/Litre.

Suitable media for use in the present invention are available from commercial suppliers such as, for example, Gibco, and JRH Biosciences.

In one embodiment, the medium is composed as shown in Table 3, optionally supplemented with one or more of the components shown in Table 4.

The table below (Table 3) is a composition of a medium suitable for use in the present invention. Optionally, one or more of the components listed in Table 4 is/are added to the culture medium. Preferred ranges are listed in Table 4. In one embodiment, the medium used is Medium 318-X; in another embodiment, it is medium CHO-K.

TABLE 3

| COMPONENT | Range (mg/L) | Concentration in CHO-K (mg/L) | Concentration in 318-X (mg/L) |
|---|---|---|---|
| Sodium chloride | 0-70,000 | 6122 | 6996 |
| Potassium chloride | 0-3118 | 311.8 | 311.8 |
| Sodium dihydrogen phosphate monohydrate | 0-625 | 62.5 | 62.5 |
| Sodium hydrogen carbonate | 0-27 | — | 2.7 |
| Disodium hydrogen phosphate anhydrous | 0-710 | 71.02 | — |
| Disodium hydrogen phosphate heptahydrate | 0-1340 | — | 134 |
| Magnesium chloride anhydrous | 0-287 | 28.64 | — |
| Magnesium chloride hexahydrate | 0-610 | — | 61 |
| Magnesium sulphate anhydrous | 0-488 | 48.84 | — |
| Magnesium sulphate heptahydrate | 0-1000 | — | 100 |
| Calcium chloride anhydrous | 0-1166 | 116.6 | 116.6 |
| Copper sulphate pentahydrate | 0-0.014 | 0.0013 | 0.0013 |
| Ferrous sulphate heptahydrate | 0-4.17 | 0.147 | 0.417 |
| Ferric nitrate nonahydrate | 0-0.5 | 0.05 | 0.05 |
| Ferric citrate | 0-123 | 0.4 | 12.24 |
| Zinc sulphate heptahydrate | 0-0.44 | 0.432 | 0.432 |
| Dextrose anhydrous | 0-45,000 | 4501 | 4500 |
| Linoleic acid | 0-12 | 1.189 | 0.336 |
| Insulin | 0-50 | 5 | 5 |
| DL 68 Thioctic Acid | 0-9 | 0.473 | 0.84 |
| L-alanine | 0-50 | 4.45 | 4.45 |
| L-arginine chloride | 0-5500 | 547.8 | 447.5 |
| L-asparagine monohydrate | 0-6010 | 407.5 | 607.5 |
| L-aspartic acid | 0-1100 | 6.65 | 106.65 |
| L-cysteine hydrochloride monohydrate | 0-1200 | 117.65 | 77.56 |
| L-glutamic acid | 0-2500 | 251.35 | 107.35 |
| Glycine | 0-190 | 18.75 | 18.75 |
| L-histidine hydrochloride monohydrate | 0-2200 | 211.48 | 101.48 |
| L-isoleucine | 0-750 | 54.47 | 74.47 |
| L-leucine | 0-1800 | 179.05 | 159.05 |
| L-lysine hydrochloride | 0-2400 | 231.25 | 131.25 |
| L-methionine | 0-1380 | 137.24 | 97.24 |
| L-phenylalanine | 0-1600 | 155.48 | 85.48 |
| L-proline | 0-1150 | 17.25 | 117.25 |
| L-serine | 0-4300 | 266.25 | 426.25 |
| L-threonine | 0-1800 | 173.45 | 73.45 |
| L-tryptophan | 0-2100 | 39.02 | 209.02 |
| L-tyrosine disodium dihydrate | 0-900 | 55.79 | 85.79 |
| L-valine | 0-1800 | 177.85 | 125.85 |
| L-cystine dihydrochloride | 0-320 | 31.29 | 31.29 |
| Sodium hypoxanthine | 0-25 | 2.39 | 2.39 |
| Putrescine dihydrochloride | 0-1 | 0.081 | 0.081 |
| Sodium pyruvate | 0-2300 | 220 | 55 |
| D-Biotin | 0-3 | 0.1313 | 0.259 |
| D-calcium pantothenate | 0-60 | 4.08 | 6 |

TABLE 3-continued

| COMPONENT | Range (mg/L) | Concentration in CHO-K (mg/L) | Concentration in 318-X (mg/L) |
|---|---|---|---|
| Folic acid | 0-70 | 4.65 | 6.65 |
| I-inositol | 0-700 | 39.1 | 65.6 |
| Nicotinamide | 0-50 | 3.085 | 4.2 |
| Choline chloride | 0-450 | 29.32 | 42 |
| Pyridoxine hydrochloride | 0-25 | 0.117 | 2.2 |
| Riboflavin | 0-3 | 0.219 | 0.219 |
| Thiamine hydrochloride | 0-35 | 2.67 | 3.17 |
| Thymidine | 0-4 | 0.365 | 0.365 |
| Vitamin B12 | 0-50 | 2.68 | 4.68 |
| Pyridoxal hydrochloride | 0-60 | 6 | 2 |
| Glutathione | 0-50 | 2.5 | 5 |
| Sodium Selenite | 0-0.5 | 0.02175 | 0.0232 |
| L-ascorbic acid | 0-50 | 27.5 | 5 |
| Pluronic F68 | 0-10,000 | 1000 | 1000 |
| Vitamin K | 0-50 | 5 | 5 |
| Dextran T 70 | 0-1000 | — | 100 |
| Soy hydrolysate (e.g., HY-SOY ®) | 0-5000 | 500 | — |

Optional Components:

TABLE 4

| Component | Range (mg/L) |
|---|---|
| Vegetable hydrolysates HyPep 4601, 4602, 4605, 5603, 7401 | 0-5000 |
| Lipids Oleic acid | 0-15 |
| Growth Factors HGR, IGF, EGF | 0-50 |

In another embodiment, the medium used has the following composition (318-U medium):

TABLE 5

| COMPONENT | mg/L |
|---|---|
| Sodium chloride | 6122 |
| Potassium chloride | 311.8 |
| Sodium dihydrogen phosphate monohydrate | 62.5 |
| Disodium hydrogen phosphate anhydrous | 71.02 |
| Magnesium chloride anhydrous | 28.64 |
| Magnesium sulphate anhydrous | 48.84 |
| Calcium chloride anhydrous | 116.6 |
| Copper sulphate pentahydrate | 0.0013 |
| Ferrous sulphate heptahydrate | 0.417 |
| Ferric nitrate nonahydrate | 0.05 |
| Zinc sulphate heptahydrate | 0.432 |
| Dextrose anhydrous | 4501 |
| Linoleic acid | 1.189 |
| DL-68-Thioctic acid | 0.473 |
| L-Alanine | 4.45 |
| L-Arginine hydrochloride | 547.5 |
| L-Asparagine monohydrate | 407.5 |
| L-Aspartic acid | 6.65 |
| L-Cysteine hydrochloride monohydrate | 117.65 |
| L-Glutamic acid | 251.35 |
| L-Glutamine | 365 |
| Glycine | 18.75 |
| L-Histidine hydrochloride monohydrate | 211.48 |
| L-Isoleucine | 54.47 |
| L-Leucine | 179.05 |
| L-Lysine hydrochloride | 231.25 |
| L-Methionine | 137.24 |
| L-Phenylalanine | 155.48 |
| L-Proline | 17.25 |

TABLE 5-continued

| COMPONENT | |
|---|---|
| L-Serine | 266.25 |
| L-Threonine | 173.45 |
| L-Tryptophan | 39.02 |
| L-Tyrosine disodium dihydrate | 55.79 |
| L-Valine | 177.85 |
| L-Cystine dihydrochloride | 31.29 |
| Sodium hypoxanthine | 2.39 |
| Putrescine dihydrochloride | 0.081 |
| Sodium pyruvate | 220 |
| D-Biotin | 0.1313 |
| D-Calcium pantothenate | 4.08 |
| Folic acid | 4.65 |
| I-Inositol | 39.1 |
| Nicotinamide | 3.085 |
| Choline chloride | 29.32 |
| Pyridoxine hydrochloride | 0.117 |
| Riboflavin | 0.219 |
| Thiamine hydrochloride | 2.67 |
| Thymidine | 0.365 |
| Vitamin B12 | 2.68 |
| Pyridoxal hydrochloride | 3 |
| Glutathione | 2.5 |
| Sodium selenite | 0.02175 |
| L-Ascorbic acid, free acid | 27.5 |
| Sodium hydrogen carbonate | 2440 |
| HySoy (soy protein hydrolysate) | 500 |
| Ethanolamin | 1.22 |
| Insulin | 5 |
| Dextran T70 | 100 |
| Pluronic F68 | 1000 |
| Vitamin K1 | 5 |
| | mL/L |
| Fe/citrat complex (50 mM/1 M) | 0.4 |
| Mercaptoethanol | 0.0035 |

The medium is preferably a medium lacking animal-derived components, or a medium lacking animal-derived components and lacking proteins ("protein-free").

In one embodiment the medium is a commercially available protein-free CHO medium lacking animal-derived components (JRH Biosciences) and the cell line is a CHO cell. In one embodiment, the medium is 318-X Medium and the cell line is a BHK cell line; in another embodiment, the medium is 318-U Medium and the cell line is a BHK cell line. In another embodiment, the medium is CHO-K Medium and the cell line is a CHO cell line.

In some embodiments, the cells used in practicing the present invention are adapted to suspension growth in medium lacking animal-derived components, such as, e.g., medium lacking serum. Such adaptation procedures are described, e.g., in Scharfenberg, et al., *Animal Cell Technology Developments towards the 21$^{st}$ Century*, E. C. Beuvery et al. (Eds.), Kluwer Academic Publishers, pp. 619-623, 1995 (BHK and CHO cells); Cruz, *Biotechnol. Tech.* 11:117-120, 1997 (insect cells); Keen, *Cytotechnol.* 17:203-211, 1995 (myeloma cells); Berg et al., *Biotechniques* 14:972-978, 1993 (human kidney 293 cells). In a particularly preferred embodiment, the host cells are BHK 21 or CHO cells that have been engineered to express human Factor VII and that have been adapted to grow in the absence of serum or animal-derived components.

Downstream Processing

Once the medium has been removed from the culture vessel, it may be subjected to one or more processing steps to obtain the desired protein, including, without limitation, centrifugation or filtration to remove cells that were not immobilized in the carriers; affinity chromatography, hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, *Protein Purification*, Springer-Verlag, New York, 1982; and *Protein Purification*, J.-C. Janson and Lars Ryden, editors, VCH Publishers, New York, 1989.

Purification of Factor VII or Factor VII-related polypeptides may involve, e.g., affinity chromatography on an anti-Factor VII antibody column (see, e.g., Wakabayashi et al., *J. Biol. Chem.* 261:11097, 1986; and Thim et al., *Biochem.* 27:7785, 1988) and activation by proteolytic cleavage, using Factor XIIa or other proteases having trypsin-like specificity, such as, e.g., Factor IXa, kallikrein, Factor Xa, and thrombin. See, e.g., Osterud et al., *Biochem.* 11:2853 (1972); Thomas, U.S. Pat. No. 4,456,591; and Hedner et al., *J. Clin. Invest.* 71:1836 (1983). Alternatively, Factor VII may be activated by passing it through an ion-exchange chromatography column, such as Mono Q® (Pharmacia) or the like.

The following examples are intended as non-limiting illustrations of the present invention.

Experimentals

General Methods

Assays Suitable for Determining Biological Activity of Factor VII Polypeptides

Factor VII polypeptides useful in accordance with the present invention may be selected by suitable assays that can be performed as simple preliminary in vitro tests. Thus, the present specification discloses a simple test (entitled "In Vitro Hydrolysis Assay") for the activity of Factor VII polypeptides.

In Vitro Hydrolysis Assay (Assay 1)

Native (wild-type) Factor VIIa and Factor VII polypeptide (both hereinafter referred to as "Factor VIIa") may be assayed for specific activities. They may also be assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM HEPES, pH 7.4, containing 0.1 M NaCl, 5 mM $CaCl_2$ and 1 mg/mL bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used for calculating the ratio between the activities of Factor VII polypeptide and wild-type Factor VIIa:

Ratio=($A$405 nm Factor VII polypeptide)/($A$405 nm Factor VIIa wild-type).

Based thereon, Factor VII polypeptides with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

The activity of the Factor VII polypeptides may also be measured using a physiological substrate such as Factor X ("In Vitro Proteolysis Assay"), suitably at a concentration of 100-1000 nM, where the Factor Xa generated is measured after the addition of a suitable chromogenic substrate (eg. S-2765). In addition, the activity assay may be run at physiological temperature.

In Vitro Proteolysis Assay (Assay 2)

Native (wild-type) Factor VIIa and Factor VII polypeptide (both hereinafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 μL 50 mM HEPES, pH 7.4, containing 0.1 M NaCl, 5 mM $CaCl_2$ and 1 mg/mL bovine serum albumin, are incubated for 15 min. Factor X cleavage is then stopped by the addition of 50 μL 50 mM HEPES, pH 7.4, containing 0.1 M NaCl, 20 mM EDTA and 1 mg/mL bovine serum albumin. The amount of Factor Xa generated is measured by the addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used for calculating the ratio between the proteolytic activities of Factor VII polypeptide and wild-type Factor VIIa:

Ratio=($A$405 nm Factor VII polypeptide)/($A$405 nm Factor VIIa wild-type).

Based thereon, Factor VII polypeptide with an activity lower than, comparable to, or higher than native Factor VIIa may be identified, such as, for example, Factor VII polypeptides where the ratio between the activity of the Factor VII polypeptide and the activity of native Factor VII (wild-type FVII) is about 1.0 versus above 1.0.

EXAMPLES

Example 1

Serum-Free Production of Factor VII

The following experiment was performed to produce Factor VII in large pilot-scale culture.

A CHO K1 cell line transformed with a Factor VII-encoding plasmid was adapted to growth in suspension culture in a medium free of animal derived components. A bank of the adapted cells was frozen. Cells from the bank were propagated in spinner bottles in suspension culture in medium free of animal derived components. As the cell number increased, the volume was gradually increased by addition of new medium. When the volume had reached 4 L, and the cell number had reached ≈$0.8*10^6$/ml, the contents of the spinner bottles were transferred into a 50 L stirred tank reactor (seed reactor). As the cell number increased in the 50 L reactor, the volume was gradually increased by addition of new medium. When the volume had reached 50 L, and the cell number had reached ≈$1\times10^6$/ml, the contents of the 50 L reactor were transferred into a 500 L stirred tank reactor (production reactor). The 500 L reactor contained macroporous Cytopore 1 carriers (Amersham Biosciences) within which the cells became immobilized within 24 hours after inoculation. The volume in the 500 L reactor was gradually increased by addition of new medium as the cell number increased. When the volume had reached 450 L, and the cell number had reached ≈$2\times10^6$/ml, the production phase was initiated and a medium change was performed every 24 hours: Agitation was stopped to allow for sedimentation of the cell-containing carriers, and 80% of the culture supernatant was then harvested and replaced with new medium. The harvested culture supernatant was filtered to remove non-trapped cells and cell debris and was then transferred for further processing. The 50 L as well as the 500 L bioreactor was instrumented for control of temperature, dissolved oxygen (sparging of oxygen through microsparger), agitation rate, headspace aeration rate and pH (downwards control by addition of $CO_2$ gas to headspace, no upwards control by addition of base). Furthermore, the 500 L bioreactor was instrumented for control of dissolved $CO_2$. Online $CO_2$ measurement was performed by means of an YSI 8500 $CO_2$-instrument. The level of $CO_2$ was controlled by sparging of atmospheric air into the liquid through a tube according to the $CO_2$ signal. The sparging rate was set to 0 L/min per L of culture liquid when the $CO_2$ concentration was at or below the set-point, and to 0.01-0.05 L/min per L of culture liquid when the $CO_2$ concentration was above the set-point. The set-point for dissolved $CO_2$ was 160 mmHg. As mentioned, no base was added to the bioreactor to control pH upwards. During the production phase the cell density reached $1-2\times10^7$ cells/ml, and the FVII concentration in the daily harvest 10-20 mg/L. The $pCO_2$ was maintained within the range of 150-170 mmHg. The pH was kept above 6.70, even though no base was added.

The invention claimed is:

1. A method for large-scale production of a polypeptide in eukaryote cells contained in a culture liquid, said method comprising: monitoring the concentration of dissolved $CO_2$ in the culture liquid, and constantly or intermittently sparging air through the culture liquid, wherein the sparging rate of the air is controlled in relation to the monitored concentration of dissolved $CO_2$ in the culture liquid.

2. The method according to claim 1, wherein the air is sparged at a rate sufficient for maintaining the concentration of dissolved $CO_2$ in the culture liquid within a predetermined range comprising a set-point for said concentration.

3. The method according to claim 2, wherein the predetermined range for the concentration of dissolved $CO_2$ is 80-200 mmHg.

4. The method according to claim 3, wherein the set-point concentration of dissolved $CO_2$ in the culture liquid is a value in the range of 100-180 mmHg.

5. The method according to claim 4, wherein the sparging rate of air is in the range of 0.000-0.100 L/min per L of culture liquid.

6. The method according to claim 5, wherein the sparging rate of air is in the range of 0.005-0.020 L/min per L of culture liquid when the monitored concentration of dissolved $CO_2$ is equal to the set-point concentration.

7. The method according to claim 6, wherein the sparging rate of air is:
   in the range of 0.000-0.005 L/min per L of culture liquid when the monitored concentration of dissolved $CO_2$ is equal to the set-point concentration−5 mmHg; and
   in the range of 0.010-0.100 L/min per L of culture liquid when the monitored concentration of dissolved $CO_2$ is equal to the set-point concentration+5 mmHg.

8. The method according to claim 1, wherein any solid or liquid substances added to the culture liquid do not give rise to a localized pH value of above 7.5 in said culture liquid.

9. The method according to claim 1, wherein the polypeptide is a Factor VII polypeptide.

10. A method for large-scale production of a polypeptide in eukaryote cells contained in a culture liquid, said method comprising constantly or intermittently sparging air through the culture liquid at a rate sufficient for maintaining the concentration of dissolved $CO_2$ in the culture liquid within a predetermined range comprising a set-point for said concentration, wherein any solid or liquid substances added to the culture liquid does not give rise to a localized pH value of above 7.5 in said culture liquid.

11. The method according to claim 10, wherein the sparging rate of air is in the range of 0.000-0.070 L/min per L of culture liquid L/min per L of culture liquid.

12. The method according to claim 10, wherein the concentration of dissolved $CO_2$ in the culture liquid is monitored.

13. The method according to claim 12, wherein the sparging rate of air is in the range of 0.005-0.020 L/min per L of culture liquid when the monitored concentration of dissolved $CO_2$ is equal to the set-point concentration.

14. The method according to claim 13, wherein the sparging rate of air is: in the range of 0.000-0.005 L/min per L of culture liquid when the monitored concentration of dissolved $CO_2$ is equal to the set-point concentration−5 mmHg; and in the range of 0.010-0.100 L/min per L of culture liquid when the monitored concentration of dissolved $CO_2$ is equal to the set-point concentration+5 mmHg.

15. The method according to claim 10, wherein the polypeptide is a Factor VII polypeptide.

* * * * *